United States Patent [19]
Dean et al.

[11] Patent Number: 6,001,991
[45] Date of Patent: Dec. 14, 1999

[54] ANTISENSE OLIGONUCLEOTIDE MODULATION OF MDR P-GLYCOPROTEIN GENE EXPRESSION

[75] Inventors: Nicholas M. Dean, Encinitas; Muthiah Manoharan, Carlsbad, both of Calif.

[73] Assignee: Isis Pharmaceuticals Inc., Carlsbad, Calif.

[21] Appl. No.: 08/940,250

[22] Filed: Sep. 30, 1997

Related U.S. Application Data

[63] Continuation-in-part of application No. 08/731,199, Oct. 4, 1996, abandoned.

[51] Int. Cl.$^6$ .............................. C07H 21/04; C12Q 1/68
[52] U.S. Cl. .................. 536/24.5; 536/23.1; 536/24.31; 435/6
[58] Field of Search .................... 536/23.1, 24.1, 536/24.5, 24.31, 24.33; 435/6, 91.1, 375, 325, 366; 514/44

[56] References Cited

U.S. PATENT DOCUMENTS

| | | | |
|---|---|---|---|
| 4,689,320 | 8/1987 | Kaji ........................................... | 514/44 |
| 4,806,463 | 2/1989 | Goodchild et al. .......................... | 435/5 |
| 5,034,506 | 7/1991 | Summerton et al. ................... | 528/391 |
| 5,087,617 | 2/1992 | Smith ........................................ | 514/44 |
| 5,098,890 | 3/1992 | Gewirtz et al. ............................ | 514/44 |
| 5,135,917 | 8/1992 | Burch ........................................ | 514/44 |
| 5,138,045 | 8/1992 | Cook et al. ............................. | 536/24.5 |
| 5,166,195 | 11/1992 | Ecker ....................................... | 514/44 |
| 5,194,428 | 3/1993 | Agrawal et al. .......................... | 514/44 |
| 5,218,105 | 6/1993 | Cook et al. .......................... | 536/25.31 |
| 5,242,906 | 9/1993 | Pagano et al. ............................. | 514/44 |
| 5,264,423 | 11/1993 | Cohen et al. .............................. | 514/44 |
| 5,276,019 | 1/1994 | Cohen et al. .............................. | 514/44 |
| 5,286,717 | 2/1994 | Cohen et al. .............................. | 514/44 |
| 5,459,255 | 10/1995 | Cook et al. .......................... | 536/27.13 |
| 5,510,239 | 4/1996 | Baracchini, Jr. et al. .................. | 435/6 |
| 5,683,987 | 11/1997 | Smith ........................................ | 514/44 |

FOREIGN PATENT DOCUMENTS

| | | |
|---|---|---|
| 95/06659 WO | 3/1995 | WIPO . |
| 9602556A2 | 2/1996 | WIPO . |

OTHER PUBLICATIONS

Akhtar et al., Cellular uptake and intracellular fate of antisense oligonucleotides. *Trends in Cell Biology*, 1992, 2, 139.

Alahari et al., "The fission yeast prp4$^+$ gene involved in pre-mRNA splicing codes for a predicted serine/threonine kinase and is essential for growth", *Nucl. Acids Res.*, 1993, 21, 4079.

Bennett et al,. "Cationic Lipids Enhance Cellular Uptake and Activity of Phosphorothioate Antisense Oligonucleotides", *Mol. Pharm.*, 1992, 41, 1023.

Berkow et al., eds., *The Merck Manual of Diagnosis and Therapy*, 15th Ed., Rahay, N.J., 1987, pp. 1206–1228.

Bradley et al., "P–glycoprotein, multidrug resistance and tumor progression", *Cancer Metastasis Rev.*, 1994, 13, 223.

Brigstock et al., "Species–Specific High Molecular Weight Forms of Basic Fibroblast Growth Factor", *Growth Factors*, 1990, 4, 45.

Chabner et al., "Reversal of Multidrug Resistance", *J. Clin. Oncol.*, 1991, 9, 4.

Chen et al., "Genomic Organization of the Human Multidrug Resistance (MDRI) Gene and Origin of P–glycoproteins", *J. Biol. Chem.*, 1990, 265, 506.

Corrias et al., "An Oligomer Complementary to the 5' End Region of MDR1 Gene Decreases Resistance to Doxorubicin of Human Adenocarcinoma–Resistant Cells", *Anticancer Res.*, 1992, 12, 1431.

Crooke et al., "Pharmacokinetic Properties of Several Novel Oligonucleotide Analogs in mice", *J. Pharmacol. Exp. Ther.*, 1996, 277, 923.

Dean et al., "Inhibition of Protein Kinase C–α Expression in Human A549 Cells by Antisense Oligonucleotides Inhibits Induction of Intercellular Adhesion Molecule 1 (ICAM–1) mRNA by Phorbol Esters", *J. Biol. Chem.*, 1994, 269.

De Virgilio et al., "Cloning and Disruption of a Gene Required for Growth on Acetate but not on Ethanol: The Acetyl–Coenzyme A Synthetase Gene of *Saccharomyces cerevisiae*", *Yeast*, 1992, 8, 1043.

Efferth et al., "Modulation of P–Glycoprotein–Mediated Multidrug Resistance by Monoclonal Antibodies, Immunotoxins of Antisense Oligodeoxynucleotides in Kidney Carcinoma and Normal Kidney Cells", *Oncol.*, 1993, 50, 303.

French et al., "Expression of Two Related Nonstructural Proteins of Bluetongue Virus (BTV) Type 10 in Insect Cells by a Recombinant Baculovirus: Production of Polyclonal Ascitic Fluid and Characterization of the Gene Product in BTV–Infected BHK Cells," *J. Virol.*, 1989, 63, 3270.

(List continued on next page.)

*Primary Examiner*—Nancy Degen
*Assistant Examiner*—Andrew Wang
*Attorney, Agent, or Firm*—Law Offices of Jane Massey Licata

[57] ABSTRACT

Oligonucleotides are provided which are specifically hybridizable with nucleic acids encoding the human MDR1 P-glycoprotein. Also disclosed are methods of using the oligonucleotides of the invention in methods of modulating the expression of MDR genes, inhibition of which leads to inhibition of the synthesis of MDR P-glycoproteins and thereby inhibits cellular multidrug resistance. Such inhibition is desirable for treating various hyperproliferative disorders or diseases, such as various cancers, in conjunction with chemotherapy utilizing one or more chemotherapeutic agents, for preventing or modulating the development of multidrug resistance during the chemotherapeutic treatment of an animal, and for resensitizing hyperproliferative MDR cells in an animal having such diseases or disorders that has been previously exposed to chemotherapeutic agents. Modified derivatives of the oligonucleotides of the invention, such as chimeras and conjugates (e.g., of an oligonucleotide and a lipophilic moiety, such as cholesterol), are also disclosed. The biological activity and cellular uptake of oligonucleotides is enhanced by such modifications.

6 Claims, 1 Drawing Sheet

OTHER PUBLICATIONS

Gao et al., "Cloning and Characterization of a Mouse Gene with Homology to the Human von Hippel–Lindau Disease Tumor Suppressor Gene: Implications for the Potential Organization of the Human von Hippel–Lindau Disease Gene", *Cancer Res.*, 1995, 55, 743.

Gelbert et al., "Analysis of GPT Activity in Mammalian Cells with a Chromosomally Integrated Shuttle Vector Containing Altered gpt Genes", *Somat. Cell. Mol. Genet.*, 1990, 16, 173.

Gold and Stormo, in : *Escherichia coli and Salmonella typhimurium: Cellular and Molecular Biology*, vol. 2, 1987, Neidhardt et al., eds., American Society for Microbiology, Washington, D.C., p. 1303.

Gottesman et al., "The Multidrug Transporter, a Double–edged Sword", *J. Biol. Chem.*, 1988, 263, 12163.

Ho et al., "Potent antisense oligonucleotides to the human multidrug resistance–1 mRNA are rationally selected by mapping RNA–accessible sites with oligonucleotide libraries", *Nucl. Acids Res.*, 1996, 24, 1901.

Ishida et al., "Multidrug Resistance in Cultured Human Leukemia and Lymphoma Cell Lines Detected by a Monoclonal Antibody, MRK16", *Jpn. J. Cancer Res.*, 1989, 80, 1006.

Kabanov et al., "A new class of antivirals: antisense oligonucleotides combined with a hydrophobic substituent effectively inhibit influenza virus reproduction and synthesis of virus–specific proteins in MDCK cells", *FEBS Lett.*, 1990, 259, 327.

Kanagasundaram et al., "Isolation and characterization of the gene encoding gluconolactonase from *Zymomonas mobilis*", *Biochim. Biophys. Acta*, 1992, 1171, 198.

Kane et al., "A new vector using the human multidrug resistance gene as a selectable marker enables overexpression of foreign genes in eukaryotic cells", *Gene*, 1989, 84, 439.

Kaji et al., "Structurally Distinct MDR Modulators Show Specific Patterns of Reversal against P–Glycoproteins Bearing Unique Mutations at Serine$^{939/941}$", *Biochem.*, 1994, 33, 5041.

Kiehntopf et al., "Ribozyme–mediated cleavage of the MDR–1 transcript restores chemosensitivity in previously resistant cancer cells", *EMBO J.*, 1994, 13, 4645.

Kobayashi et al., "Reversal of Drug Sensitivity in Multidrug–Resistant Tumor Cells by an MDR1 (PGY1) Ribozyme", *Cancer Res.*, 1994, 54, 1271.

Krieg et al., "Modification of antisense phosphodiester oligodeoxynucleotides by a 5' cholesteryl moiety increases cellular assocation and improves efficacy", *Proc. Natl. Acad. Sci. USA*, 1993, 90, 1048.

Letsinger et al., *Proc. Natl. Acad. Sci. USA*, 1989, 86, 6553.

MacKellar et al., "Synthesis and physical properties of anti–HIV antisense oligonucleotides bearing terminal lipophilic groups", *Nucl. Acids Res.*, 1992, 20, 3411.

Manoharan et al., "Introduction of a Lipophilic Thioether Tether in the Minor Groove of Nucleic Acids for Antisense Applications", *Bioorg. Med. Chem. Let.*, 1993, 3, 2765.

Manoharan et al., "Lipidic Nucleic Acids", *Tetrahedron Lett.*, 1995, 36, 3651.

Manoharan et al., "Oligonucleotide Conjugates: Alteration of the Pharmacokinetic Properties of Antisense Agents", *Nucleosides & Nucleotides*, 1995, 14, 969.

Manoharan et al., "Cholic Acid–Oligonucleotide Conjugates for Antisense Applications", *Bioorg. Med. Chem. Let.*, 1994, 4, 1053.

Manoharan et al., "Chemical Modifications to Improve Uptake and Bioavailability of Antisense Oligonucleotides", *Ann. N.Y. Acad. Sci.*, 1992, 660, 306.

Martin et al., "Ein neuer Zugang zu 2'–O–AlkyIribonucleosiden und Eigenschaften deren Oligonucleotide", *Helv. Chim. Acta*, 1995, 78, 486.

Markussen et al., "Translational control of oskar generates Short OSK, the isoform that induces pole plasm assembly", *Development*, 1995, 121, 3723.

McDermott et al., "Structure and lens expression of the gene encoding chicken βA3/A1–crystallin", *Gene*, 1992, 117, 193.

Mishra et al., "Improved leishmanicidal effect of phosphorotioate antisense oligonucleotides by LDL–mediated delivery", *Biochim. Biophys. Acta*, 1995, 1264, 229.

Monaco et al., "Structure of Two Rat Genes Coding for Closely Related Rolipram–sensitive cAMP Phosphodiesterases", *J. Biol. Chem.*, 1994, 269, 347.

Nielsen et al., "Sequence–Selective Recognition of DNA by Strand Displacement with a Thymine–Substituted Polyamide", *Science*, 1991, 254, 1497.

Oberhauser et al., "Effective incorporation of 2'–O–methyl–oligoribonucleotides into liposomes and enhanced cell assocation through modification with thiocholesterol", *Nucl. Acids. Res.*, 1992, 20, 533.

Olsen et al., "Inhibition of Protein Kinase–A by Overexpression of the Cloned Human Protein Kinase Inhibitor", *Mol. Endocrinol.*, 1991, 5, 1246.

Palfner et al., "Improvement of Hammerhead Ribozymes Cleaving mdr–1 RNA", *Biol. Chem. Hoppe–Seyler*, 1995, 376, 289.

Perri et al., "Interactions of Plasmid–encoded Replication Intitiation Proteins with the Origin of DNA Replication in the Broad Host Range Plasmid RK2", *J. Biol. Chem.*, 1991, 266, 12536.

Pushpa–Rekha et al., "Rat Phospholipid–hydroperoxide Glutathione Peroxidase", *J. Biol. Chem.*, 1995, 270, 26993.

Richart et al., "Stability and Covalent Modification of P–Glycoprotein in Multidrug–Resistant KB Cells", *Biochem.*, 1988, 28, 7607.

Rogers et al., "Alternative splicing dictates translational start in Epstein–Barr virus transcripts", *EMBO J.*, 1990, 9, 2273.

Roninson, "The Role of the MDR1 (P–Glycoprotein) Gene in Multidrug Resistance In Vitro and In Vivo", *Biochem. Pharmacol.*, 1992, 43, 95.

Saison–Behmoaras et al., "Short modified antisense oligonucleotides directed against Ha–ras point mutation induce selective cleavage of the mRNA and inhibit T24 cells proliferation", *EMBO J.*, 1991, 10, 111.

Sambrook et al., *Molecular Cloning. A Laboratory Manual*, Cold Spring Harbor Laboratory Press, 1989, vol. 2, p. 10.59.

Saul et al., "celB, a Gene Coding for a Bifunctional Cellulase from the Extreme Thermophile "*Caldocellum saccharolyticum*"", *Appl. Environ. Microbiol.*, 1990, 56, 3117.

Scanlon et al., "Ribozyme–mediated reversal of the multidrug–resistant phenotype", *Proc. Natl. Acad. Sci. USA*, 1994, 91, 11123.

Shea et al., "Synthesis, hybridization properties and antiviral activity of lipid–oligodeoxynucleotide conjugates", *Nucl. Acids Res.*, 1990, 18, 3777.

Shoji et al., "Mechanism of cellular uptake of modified oligodeoxynucleotides containing methylphosphonate linkages", *Nucl. Acids Res.*, 1991, 19, 5543.

Svinarchuk et al., "Inhibition of HIV proliferation in MT–4 cells by antisense oligonucleotide conjugated to lipophilic groups", *Biochimie*, 1993, 75, 49.

Thierry et al., "Overcoming multidrug resistance in human tumor cells using free and liposomally encapsulated antisense oligodeoxynucleotides", *Biochem. Biophys. Res. Commun.*, 1993, 190, 952.

Twentyman et al., "A Comparison of Rhodamine 123 Accumulation and Efflux in Cells with P–Glycoprotein–mediated and MRP–associated Multidrug Resistance Phentypes", *Eur. J. Cancer*, 1994, 30, 1360.

Vasanthakumar et al., "Modulation of Drug Resistance in a Daunorubicin Resistant Subline with Oligonucleoside Methylphosphonates", *Cancer Commun.*, 1989, 1, 225.

Yaoita et al., "*Xenopus laevis* $\alpha$ and $\beta$ thyroid hormone receptors", *Proc. Natl. Acad. Sci. USA*, 1990, 87, 7090.

* 11439, 11440, 11441, 11442

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 1:

GAGCCGCTAC TCGAATGAGC                                           20

(2) INFORMATION FOR SEQ ID NO: 2:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 2:

GTTCTGGCTT CCGTTGCACC                                           20

(2) INFORMATION FOR SEQ ID NO: 3:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 3:

CCCGGCCCGG ATTGACTGAA                                           20

(2) INFORMATION FOR SEQ ID NO: 4:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 4:

CCATCCCGAC CTCGCGCTCC                                           20

(2) INFORMATION FOR SEQ ID NO: 5:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 5:

```
CGGTCCCCTT CAAGATCCAT                                               20

(2) INFORMATION FOR SEQ ID NO: 6:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 6:

CCCCTTCAAG ATCCATCCCG                                               20

(2) INFORMATION FOR SEQ ID NO: 7:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 7:

CAAGATCCAT CCCGACCTCG                                               20

(2) INFORMATION FOR SEQ ID NO: 8:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 8:

CCTGGTCATG TCTTCCTCCA                                               20

(2) INFORMATION FOR SEQ ID NO: 9:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 9:

CTTTGCCCAG ACAGCAGCTG                                               20

(2) INFORMATION FOR SEQ ID NO: 10:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 10:

GTTCACTGGC GCTTTGTTCC                                               20

(2) INFORMATION FOR SEQ ID NO: 11:
```

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 11:

TGAACTTGAC TGAGGAAATG                                                    20

(2) INFORMATION FOR SEQ ID NO: 12:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 12:

CTTGGAAGAG CCGCTACTCG                                                    20

(2) INFORMATION FOR SEQ ID NO: 13:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 13:

GCCGCTACTC GAATGAGCGC                                                    20

(2) INFORMATION FOR SEQ ID NO: 14:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 14:

GGAAGAGCCG CTACTCGAAT                                                    20

(2) INFORMATION FOR SEQ ID NO: 15:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 15:

CTCTGTTCCT TTAATTACGA                                                    20

(2) INFORMATION FOR SEQ ID NO: 16:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 16:

TCCACTTGAT GATGTCTCTC                                              20

(2) INFORMATION FOR SEQ ID NO: 17:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 17:

CTATGATTTC TCTCCACTTG                                              20

(2) INFORMATION FOR SEQ ID NO: 18:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 18:

GGCAGTCAGT TACAGTCCAA                                              20

(2) INFORMATION FOR SEQ ID NO: 19:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 19:

TTTTAGCAAG GCAGTCAGTT                                              20

(2) INFORMATION FOR SEQ ID NO: 20:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 20:

TGCAAACATT TCAATACTTT                                              20

(2) INFORMATION FOR SEQ ID NO: 21:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 21:

```
AAGTTTAGTT TTATTATAGA                                                    20

(2) INFORMATION FOR SEQ ID NO: 22:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: No (xi) SEQUENCE DESCRIPTION:  SEQ ID NO: 22:

CACCACCCCC CTCGCTGGTC                                                    20

(2) INFORMATION FOR SEQ ID NO: 23:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: No (xi) SEQUENCE DESCRIPTION:  SEQ ID NO: 23:

CTCCCGCACA TCTCCGCGCC                                                    20

(2) INFORMATION FOR SEQ ID NO: 24:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION:  SEQ ID NO: 24:

GCCACCGTCT GCCCACTCTG                                                    20

(2) INFORMATION FOR SEQ ID NO: 25:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION:  SEQ ID NO: 25:

GGCACGTGCA ATGGCGATCC                                                    20

(2) INFORMATION FOR SEQ ID NO: 26:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION:  SEQ ID NO: 26:

CGGAGCCGCT TGGTGAGGAT                                                    20

(2) INFORMATION FOR SEQ ID NO: 27:
```

```
    (i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 27:

AGCAGCATCA TTGGCGAGCC                                               20

(2) INFORMATION FOR SEQ ID NO: 28:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

CGGCCATGGC ACCAAAGACA                                               20

(2) INFORMATION FOR SEQ ID NO: 29:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 29:

TGAACTGACT TGCCCCACGG                                               20

(2) INFORMATION FOR SEQ ID NO: 30:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 30:

GGGATGTCCG GTCGGGTGGG                                               20

(2) INFORMATION FOR SEQ ID NO: 31:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

TGCCCACCAG AGCCAGCGTC                                               20

(2) INFORMATION FOR SEQ ID NO: 32:

(i) SEQUENCE CHARACTERISTICS:
        (A) LENGTH: 20
        (B) TYPE: Nucleic Acid
        (C) STRANDEDNESS: Single
        (D) TOPOLOGY: Linear
```

(iv) ANTI-SENSE: Yes (xi) SEQUENCE DESCRIPTION: SEQ ID NO: 32:

ATGCCCAGGT GTGCTCGGAG                    20

(2) INFORMATION FOR SEQ ID NO: 33:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 33:

GCCTCCTTTG CTGCCCTCAC                    20

(2) INFORMATION FOR SEQ ID NO: 34:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 34:

TGGTGGACAG GCGGTGAGCA                    20

(2) INFORMATION FOR SEQ ID NO: 35:

(i) SEQUENCE CHARACTERISTICS:
             (A) LENGTH: 30
             (B) TYPE: Nucleic Acid
             (C) STRANDEDNESS: Single
             (D) TOPOLOGY: Linear (iv) ANTI-SENSE: No (xi) SEQUENCE DESCRIPTION: SEQ ID NO: 35:

GGATCTTGAA GGGGACCGCA ATGGAGGAGC                    30

(2) INFORMATION FOR SEQ ID NO: 36:

(i) SEQUENCE CHARACTERISTICS:
             (A) LENGTH: 30
             (B) TYPE: Nucleic Acid
             (C) STRANDEDNESS: Single
             (D) TOPOLOGY: Linear (iv) ANTI-SENSE: Yes (xi) SEQUENCE DESCRIPTION: SEQ ID NO: 36:

GTCCAACACT AAAAGCCCCA ATTAATACAG                    30

(2) INFORMATION FOR SEQ ID NO: 37:

(i) SEQUENCE CHARACTERISTICS:
             (A) LENGTH: 20
             (B) TYPE: Nucleic Acid
             (C) STRANDEDNESS: Single
             (D) TOPOLOGY: Linear (iv) ANTI-SENSE: No (xi) SEQUENCE DESCRIPTION: SEQ ID NO: 37:

-continued

```
CTTACCCGCT TGTGTTGCTG                                               20

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

CACCACCCCC CTCGCUGGUC                                               20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

CCAUCCCGAC CTCGCGCUCC                                               20

(2) INFORMATION FOR SEQ ID NO: 40:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

GUUCACTGGC GCTTTGUUCC                                               20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

CUUACCCGCT TGTGTUGGUC                                               20
```

ANTISENSE OLIGONUCLEOTIDE MODULATION OF MDR P-GLYCOPROTEIN GENE EXPRESSION

The instant application is a continuation-in-part of application Ser. No. 08/731,199, filed Oct. 4, 1996, now abandoned.

INTRODUCTION

The invention described herein was supported in part by government funding from the National Institutes of Health, Grant No. CA68790-01. Therefore, the U.S. government may have certain rights in the invention disclosed herein.

FIELD OF THE INVENTION

The present invention provides compositions and methods for modulating the expression of multidrug resistance (MDR) genes, which encode members of a family of membrane proteins (P-glycoproteins) that function as ATP driven efflux pumps. Hyperproliferative cells may become resistant to anticancer agents due to an overabundance of one or more nucleic acids (i.e., mRNA or DNA) encoding one or more such MDR proteins. By modulating this resistance according to the compositions and methods of the present invention, resistant cells are resensitized to such anticancer agents. Accordingly, the compositions and methods of the invention act to enhance the treatment of abnormal cell proliferation and tumor formation with anticancer agents. This invention also relates to diagnostics and research reagents for disease states or disorders characterized by a greater than normal amount of one or more nucleic acids encoding an MDR protein. In particular, this invention relates to antisense oligonucleotides specifically hybridizable with nucleic acids encoding the human MDR1 P-glycoprotein. These oligonucleotides have been found to modulate the expression of MDR1. Prophylactic, palliative and therapeutic effects result from such modulation. Methods for the conjugation of a lipophilic moiety, such as cholesterol, to a 3' cytidine in an oligonucleotide via an alkylamino linker are also disclosed. The biological activity and cellular uptake of oligonucleotides is enhanced by such modifications.

BACKGROUND OF THE INVENTION

Mammalian cells selected for resistance to certain antitumor drugs often display cross resistance to other apparently unrelated drugs and are thus said to display a multidrug resistant (MDR) phenotype (Bradley et al., *Cancer Metastasis Rev.*, 1994, 13, 223). One form of the MDR phenotype is based on overexpression of one or more members of a family of membrane proteins (P-glycoproteins) which serve as ATP driven drug efflux pumps (Bradley et al., *Cancer Metastasis Rev.*, 1994, 13, 223; Gottesman et al., *J. Biol. Chem.*, 1988, 263, 12163; Roninson, *Biochem. Pharmacol.*, 1992, 43, 95). The human MDR (P-glycoprotein) gene family has two members, only one of which (P170, encoded by the MDR1 gene) appears to be responsible for resistance to cytotoxic drugs (Roninson, *Biochem. Pharmacol.*, 1992, 43, 95). In highly drug-resistant cells, P-glycoprotein message and protein levels can be many times greater than in their drug sensitive counterparts. Although MDR can be modulated by using a variety of agents that competitively inhibit P-glycoprotein mediated antitumor drug efflux (Kaji et al., *Biochem.*, 1994, 33, 5041), several of these agents have proven less than ideal in clinical trials (Chabner et al., *J. Clin. Oncol.*, 1991, 9, 4). Attempts have been made to utilize a ribozyme approach to modulation of the MDR phenotype (Kiehntopf et al., *EMBO J.*, 1994, 13, 4645; Kobayashi et al., *Cancer Res.*, 1994, 54, 1271; Scanlon et al., *Proc. Natl. Acad. Sci. USA*, 1994, 91, 11123). In these efforts, however, ribozymes were introduced into cells by transfection, and clones were selected that had substantial levels of ribozyme expression. In these selected clones, a substantial impact on MDR1 mRNA and protein expression was observed. It remains to be seen whether the ribozyme approach offers a viable modality for modulating MDR expression in cell populations or tissues.

Chen et al. (*J. Biol. Chem.*, 1990, 265, 506) describe the genomic organization and nucleotide sequence of a human MDR1 gene.

Vasanthakumar et al. (*Cancer Commun.*, 1989, 1, 225) describe partial modulation of MDR1 expression, and a partial decrease in drug resistance, by methylphosphonate oligonucleotides complementary to the MDR1 gene. Neither cholesterol conjugates nor 2'-methoxyethoxy derivatives of such oligonucleotides are disclosed by Vasanthakumar et al.

Corrias et al. (*Anticancer Res.*, 1992, 12, 1431) describe unmodified oligonucleotides that modulate MDR1 expression in cultured human adenocarcinoma cell lines. Neither cholesterol conjugates nor 2'-methoxyethoxy derivatives of such oligonucleotides are disclosed by Corrias et al.

Thierry et al. (*Biochem. Biophys. Res. Commun.*, 1993, 190, 952) describe partial modulation of MDR1 expression by methylphosphonate oligonucleotides complementary to the 5' end of the coding region of the MDR1 gene. Neither cholesterol conjugates nor 2'-methoxyethoxy derivatives of such oligonucleotides are disclosed by Thierry et al.

Efferth et al. (*Oncol.*, 1993, 50, 303) describe modulation of P-glycoproteins in cell lines derived from patients with kidney tumors by monoclonal antibodies, immunotoxins and a phosphorothioate antisense oligonucleotide targeted to nucleotides −9 to +6 of the MDR1 gene. Neither cholesterol conjugates nor 2'-methoxyethoxy derivatives of the oligonucleotide are disclosed by Efferth et al.

Palfner et al. (*Biol. Chem. Hoppe-Seyler*, 1995, 376, 289) describe in vitro studies of hammerhead ribozymes capable of cleaving MDR1 mRNA molecules.

Ho et al. (*Nucl. Acids Res.*, 1996, 24, 1901) describe phosphothioate oligonucleotides that modulate RNase H activity on MDR1 RNA molecules transcribed in vitro. Neither cholesterol conjugates nor 2'-methoxyethoxy derivatives of such oligonucleotides are disclosed by Ho et al.

International Publication No. WO/9602556(A2) by Smyth describes antisense oligonucleotides to two portions of the MDR1 gene that encode nucleotide binding polypeptide motifs. Neither cholesterol conjugates nor 2'-methoxyethoxy derivatives of such oligonucleotides are disclosed by Smyth.

U.S. Pat. No. 5,510,239 to Baracchini, Jr., et al. (issued Apr. 23, 1996) describes compositions and methods for the modulation of a multidrug resistance-associated protein, MRP, which is encoded by a different gene from the target of the present invention.

To date, there are no known therapeutic agents which effectively inhibit expression of MDR genes encoding P-glycoproteins. Consequently, there remains a need for compositions and methods that effectively inhibit expression of such genes.

SUMMARY OF THE INVENTION

In accordance with the present invention oligonucleotides are provided which specifically hybridize with nucleic acids encoding an MDR P-glycoprotein. Certain oligonucleotides of the invention are designed to bind either directly to mRNA transcribed from, or to a selected DNA portion of, the human MDR1 gene, thereby modulating the amount of protein translated from MDR1 mRNA or the amount of mRNA transcribed from the MDR1 gene, respectively.

Oligonucleotides may comprise nucleotide sequences sufficient in identity and number to effect specific hybridization with a particular nucleic acid. Such oligonucleotides are commonly described as "antisense." Antisense oligonucleotides may be used as research tools, diagnostic aids, and therapeutic agents.

It has been discovered that MDR genes encoding MDR P-glycoproteins are particularly useful for this approach. Inhibition of the expression of such MDR genes leads to inhibition of the synthesis of MDR P-glycoproteins and thereby inhibits cellular multidrug resistance. Such inhibition is desirable for treating various hyperproliferative disorders or diseases, such as various cancers, in conjunction with therapy utilizing one or more chemotherapeutic agents, for preventing or modulating the development of multidrug resistance during the chemotherapeutic treatment of an animal, and for resensitizing hyperproliferative MDR cells in an animal that has been previously exposed to chemotherapeutic agents.

Methods of modulating the expression of MDR P-glycoproteins comprising contacting animals with oligonucleotides specifically hybridizable with an MDR gene are herein provided. These methods are believed to be useful both therapeutically and diagnostically as a consequence of the association between MDR expression and the multidrug resistance of hyperproliferative cells. These methods are also useful as tools, for example, in the detection and determination of the role of MDR P-glycoprotein expression in various cell functions and physiological processes and conditions, and for the diagnosis of conditions associated with such expression.

The present invention also comprises methods of inhibiting MDR-associated hyperproliferation of cells using oligonucleotides of the invention. Methods of treating abnormal proliferative conditions are also provided. These methods employ oligonucleotides of the invention. These methods are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

DETAILED DESCRIPTION OF THE INVENTION

Figure 1:
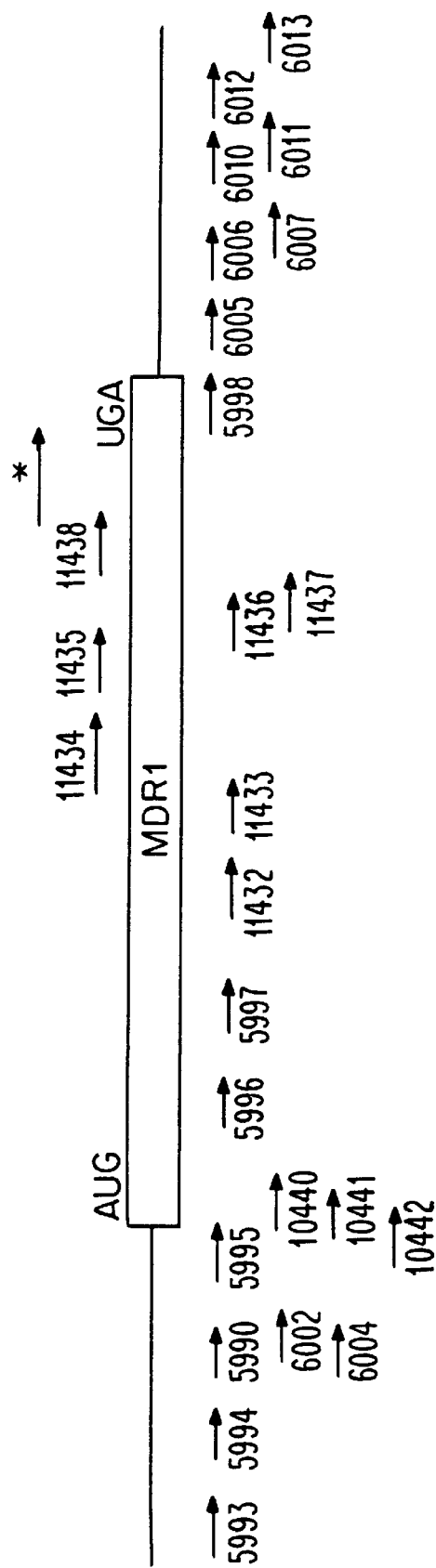
FIG. 1 schematically shows the sites of binding of antisense compounds of the present invention. Nucleotide sequences of the exemplified antisense compounds are given in Table I.

The present invention employs oligonucleotides for use in antisense inhibition of the function of RNA and DNA encoding proteins. The present invention also employs oligonucleotides which are designed to be specifically hybridizable to DNA or messenger RNA (mRNA) encoding MDR P-glycoproteins and ultimately modulating the amount of such P-glycoproteins transcribed from their respective MDR genes. Such hybridization with mRNA interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of such MDR P-glycoproteins. In the context of this invention, "modulation" means either an increase (stimulation) or a decrease (inhibition) in the expression of a gene. In the context of the present invention, inhibition is the preferred form of modulation of gene expression.

Oligonucleotides may comprise nucleotide sequences sufficient in identity and number to effect specific hybridization with a particular nucleic acid. Such oligonucleotides are commonly described as "antisense." Oligonucleotides are commonly used as research reagents and diagnostics. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed for research use.

The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to CMV. U.S. Pat. No. 5,098,890 provides oligonucleotides complementary to at least a portion of the mRNA transcript of the human c-myb U.S. Pat. No. 5,242,906 provides antisense oligonucleotides useful in the treatment of latent EBV infections.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with resistance to chemotherapeutic agents. The targeting process also includes determination of a site or sites within this gene for the oligonucleotide interaction to occur such that the desired effect, either detection or modulation of expression of the protein, will result. Within the context of the present invention, a preferred intragenic site is the region encompassing the translation initiation or termination codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors*, 1990, 4, 45; Gelbert et al., Somat. *Cell. Mol. Genet.*, 1990, 16, 173; Gold and Stormo, in: *Escherichia coli* and *Salmonella typhimurium*: Cellular and *Molecular Biology*, Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., *Development*, 1995, 121, 3723; Gao et al., *Cancer Res.*, 1995, 55, 743; McDermott et al., *Gene*, 1992, 117, 193; Perri et al., *J. Biol. Chem.*, 1991, 266, 12536; French et al., *J. Virol.*, 1989, 63, 3270; Pushpa-Rekha et al., *J. Biol. Chem.*, 1995, 270, 26993; Monaco et al.,*J. Biol. Chem.*, 1994, 269, 347; DeVirgilio et al., *Yeast*, 1992, 8, 1043; Kanagasundaram et al., *Biochim. Biophys. Acta*, 1992, 1171, 198; Olsen et al., *Mol. Endocrinol.*, 1991, 5, 1246; Saul et al., *Appl. Environ. Microbiol.*, 1990, 56, 3117; Yaoita et al., *Proc. Natl. Acad. Sci. USA*, 1990, 87, 7090; Rogers et al., *EMBO J.*, 1990, 9, 2273). In the context of the invention, "start codon" and "translation initiation codon" refer to the codon or codons that are used in vivo to initiate translation of an mRNA molecule transcribed from a gene encoding an MDR P-glycoprotein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Once the start codon region, or other target site, has been identified, oligonucleotides are chosen which are sufficiently complementary to the target, i.e., hybridize sufficiently well and with sufficient specificity to give the desired effect.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254, 1497). Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'—O—$CH_2CH_2OCH_3$, also known as 2'-O-(2-methoxyethyl)] (Martin et al., *Helv. Chim. Acta*, 1995, 78, 486). Other preferred modifications include 2'-methoxy (2'—O—$CH_3$), 2'-propoxy (2'—$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group. Base modifications or substitutions (e.g., with a "universal" base such as inosine) may also be included.

Another preferred modification of the oligonucleotides of the invention involves chemically linking to the oligonucleotide one or more lipophilic moieties which enhance the cellular uptake of the oligonucleotide. Such lipophilic moieties include but are not limited to a cholesterol moiety, a cholesteryl moiety (Letsinger et al., *Proc. Natl. Acad. Sci. USA*, 1989, 86, 6553), cholic acid (Manoharan et al.,*Bioorg. Med. Chem. Let.*, 1994, 4, 1053), a thioether, e.g., hexyl-S-tritylthiol (Manoharan et al.,*Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 35 1996, 277, 923). Oligonucleotides comprising lipophilic moieties, and methods for preparing such oligonucleotides are known in the art, for example, U.S. Pat. No. 5,138,045, No. 5,218, 105 and No. 5,459,255.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art.

The oligonucleotides in accordance with this invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage.

The oligonucleotides used in accordance with this invention may be conveniently and routinely made through the well-known technique of solid phase synthesis. Equipment for such synthesis is sold by several vendors including, for example, Applied Biosystems (Foster City, Calif.) . Any other means for such synthesis known in the art may additionally or alternatively be employed. It is also known to use similar techniques to prepare other oligonucleotides such as the phosphorothioates and alkylated derivatives.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be utilized as diagnostics, therapeutics and as research reagents and kits. For therapeutics, an animal suspected of having a disease or disorder which can be treated by modulating the expression of MDR P-glycoproteins is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier.

The oligonucleotides of the present invention can be used as diagnostics for the presence of MDR-specific nucleic acids in a cell or tissue sample. For example, radiolabeled oligonucleotides can be prepared by $^{32}$P labeling at the 5' end with polynucleotide kinase. (Sambrook et al., *Molecular Cloning. A Laboratory Manual*, Cold Spring Harbor Laboratory Press, 1989, Volume 2, pg. 10.59.) Radiolabeled oligonucleotides are then contacted with cell or tissue samples suspected of containing MDR message RNAs (and thus, P-glycoproteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing an MDR gene. Quantitation of the silver grains permits detection of the expression of mRNA molecules encoding these proteins and permits targeting of oligonucleotides to these areas.

Analogous assays for fluorescent detection of expression of MDR P-glycoproteins can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va.

The present invention employs oligonucleotides targeted to nucleic acids encoding MDR P-glycoproteins, and oligonucleotides targeted to nucleic acids encoding such proteins. Kits for detecting the presence or absence of MDR expression may also be prepared. Such kits include an oligonucleotide targeted to an MDR gene encoding a P-glycoprotein. Such kit and assay formats are known in the art.

Oligonucleotides of the present invention directed to an MDR P-glycoprotein can also be used in diagnostics, therapeutics, prophylaxis, and as research reagents and kits. Because these oligonucleotides hybridize to nucleic acids encoding MDR P-glycoproteins, sandwich and other assays can easily be constructed to exploit this fact. Hybridization of the oligonucleotides of the invention with a nucleic acid encoding an MDR P-glycoprotein can be detected by means known in the art. Such means may include conjugation of an enzyme to the oligonucleotide, radiolabelling of the oligonucleotide or any other suitable detection systems. Kits for detecting the presence or absence of may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 $\mu$g to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for cancer treatment. Examples of such chemotherapeutic agents include but are not limited to daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206–1228). When used with the compounds of the invention, such chemotherapeutic agents may be used individually, sequentially (e.g., 5-FU for a period of time followed by MTX), or in combination with one or more other such chemotherapeutic agents (e.g., 5-FU and MTX, or 5-FU and radiotherapy).

Following successful treatment, it may be desirable to have the patient undergo maintenance therapy to prevent the recurrence of the disease state, wherein the oligonucleotide is administered in maintenance doses, ranging from 0.01 $\mu$g to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 $\mu$g to 100 g per kg of body weight, and may be given once or more daily, weekly, monthly or yearly, or even once every 2 to 20 years.

The following examples illustrate the present invention and are not intended to limit the same.

EXAMPLES

Example 1

Synthesis of Oligonucleotides

Oligonucleotides were synthesized on an automated DNA synthesizer using standard phosphoramidite chemistry with oxidation using iodine. Beta-cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages. After cleavage from the controlled pore glass (CPG) column (Applied Biosystems) and deblocking in concentrated ammonium hydroxide, at 55° C. for 18 hours, the oligonucleotides were purified by precipitation (2×) from 0.5 M NaCl with 2.5 volumes of ethanol. Analytical gel electrophoresis was accomplished in 20% acrylamide, 8 M urea and 45 mM Tris-borate buffer (pH 7). Phosphorothioate oligonucleotides, and 2'-O-methyl phosphorothioate oligonucleotides, were synthesized at ISIS Pharmaceuticals using previously described procedures (Dean et al., *J. Biol. Chem.*, 1994, 269, 16416). Oligonucleotide sequences are shown in Table I, and the positions of oligonucleotides within the MDR1 gene are shown schematically in FIG. 1.

5'-cholesterol conjugated oligonucleotides were synthesized as follows. Cholesterol-3-carboxyaminohexyl-B-cyanoethyl-N, N-diisiopropyl-phosphoramidite was synthesized according to the procedure reported by MacKellar et al. (*Nucl. Acids Res.*, 1992, 20, 3411). 7.25 grams of this amidite was dissolved in anhydrous dichloromethane to bring the concentration to 0.1 M. Using this solution, ISIS 11073, a 5' cholesterol conjugated version of ISIS 5995, was synthesized by standard phosphoramidite chemistry to make an oligomer with a phosphorothioate backbone. For the cholesterol amidite coupling step, reaction time was extended to 45 minutes. This resulted in 85% coupling for the cholesterol amidite. After standard deprotection, the oligonucleotide-cholesterol conjugate was purified on a C-4 reverse-phase HPLC column (Manoharan et al., *Tetrahedron Lett.*, 1995, 36, 3651). ISIS 12064, a 5' cholesterol conjugated version of ISIS 10221, was synthesized and purified in the same manner.

Oligonucleotides comprising a 3'-O-alkylamino cholesterol moiety were prepared in the following manner. 3'-O-(propylthalimide)-cytidine was prepared essentially according to Examples 75 and 104 of WO 95/06659 (PCT/US94/10131, published Mar. 9, 1995), with the exception that N-(5-bromopentyl)phthalimide was used in place of N-(3-bromopropyl)phthalimide in order to generate 3'-O-(pentylphthlamide)-cytidine. From this compound, 5'-O-[dimethoxytrityl]-3'-O-[pentylamino]-cytidine was prepared by refluxing with hydrazine in methanol solvent. The product was purified in a silica column using 98% methanol/ ammonium hydroxide 2% solvent. 5'-O-[dimethoxytrityl]-3'-O-[pentylamino]-cytidine (1.5 g) was then treated with cholesterol chloroformate (1.1 g) in a mixture of 10 ml pyridine in 30 ml methylene chloride. After overnight stirring another 600 mg of cholesterol chloroformate was added and the reaction mixture was stirred for another four hours. Thin layer chromatography analysis showed reaction products at exocyclic amine and at 3'-O-pentylamine side chain. The desired product, 3'-O-[pentylamino-carbonyl-oxy cholesteryl]-cytidine was obtained as the slower moving product in 43% yield.

600 mg of 3'-O-[pentylamino-carbonyl-oxy cholesteryl]-cytidine was coevaporated with pyridine (2×10 ml) and then dissolved in 10 ml of anhydrous pyridine. With external cooling using a ice bath, trimethylsilyl chloride (1 ml) was added using a syringe over a period of 5 minutes and the solution was stirred for 30 minutes. Then benzoylchloride (1 ml) was added followed by 10 ml of pyridine. The reaction mixture was stirred at room temperature overnight. 4 ml of water was added with external cooling and after 30 minutes 4 ml of concentrated ammonium hydroxide (30%) was added. Stirring was continued for another 1 hour. The reaction mixture was then evaporated and extracted between methylene chloride and water. The methylene chloride layer was evaporated to give 1.2 g of crude $N^4$-benzoyl-3-O-[pentylamino carbonyl-oxy-cholesteryl]-cytidine which was then purified in a silica column using 2.5% methanol in chloroform. The product identity and homogeneity were confirmed by $^{13}C$ and $^1H$ NMR spectral studies.

$N^4$-benzoyl-3-O-[pentylamino carbonyl-oxy-cholesteryl]-cytidine (450 mg) was added to 2 g of controlled pore glass (CPG, succinylated and capped), and to this mixture 200 mg of dimethylaminopyridine, 1 g of EDC [1-ethyl-3-dimethylaminopropyl)carbodiimide hydrochloride), 400 µl of triethylamine and 10 ml pyridine were added. The mixture was shaken in a wrist-action shaker overnight. The CPG was then filtered, washed with methylene chloride, methanol, methylene chloride and then ether. Then, 1.5 g of pentachlorophenol, 1 g EDC, 1 ml of triethylamine and 10 ml of pyridine were added to the CPG and the shaking was continued for 16 hours. Then 3 ml of pyperidine was added and shaking continued for 5 minutes. The CPG was filtered, washed and dried. 9 mg of the derivatized CPS was treated with 25 ml of 2% dichloroacetic acid in methylenechloride and the loading was determined to be 27.16 µm ol/g using colorimetric assays. ISIS 13328 (GATCC*, where "C*" indicates the 3'-O-alkylamino cholesterol cytidine residue; used for NMR studies), ISIS 13329, ISIS 13330, ISIS 13331 and ISIS 13332 were synthesized using this CPG. Other 3'-O-alkylamino cholesterol derivatives, and 5'-fluorescein isothiocyanate (FITC) conjugates of the oligonucleotides of the invention are prepared in like manner using the methods disclosed in WO 95/06659 and the above protocols.

TABLE I

Oligonucleotides targeted to MDR1

| ISIS # | SEQUENCES* (DESCRIPTION) | SEQ ID NO: | TARGET REGION |
|---|---|---|---|
| 5990 | GAG-CCG-CTA-CTC-GAA-TGA-GC | 1 | 5' Untranslated |
| 5993 | GTT-CTG-GCT-TCC-GTT-GCA-CC | 2 | 5' Untranslated |
| 5994 | CCC-GGC-CCG-GAT-TGA-CTG-AA | 3 | 5' Untranslated |
| 5995 | CCA-TCC-CGA-CCT-CGC-GCT-CC | 4 | Start codon |
| 10440 | CGG-TCC-CCT-TCA-AGA-TCC-AT | 5 | Start codon |
| 10441 | CCC-CTT-CAA-GAT-CCA-TCC-CG | 6 | Start codon |
| 10442 | CAA-GAT-CCA-TCC-CGA-CCT-CG | 7 | Start codon |
| 5996 | CCT-GGT-CAT-GTC-TTC-CTC-CA | 8 | ORF** (splice junction) |
| 5997 | CTT-TGC-CCA-GAC-AGC-AGC-TG | 9 | ORF (splice junction) |
| 5998 | GTT-CAC-TGG-CGC-TTT-GTT-CC | 10 | ORF / Stop codon |
| 5999 | TGA-ACT-TGA-CTG-AGG-AAA-TG | 11 | 3' Untranslated |
| 6002 | CTT-GGA-AGA-GCC-GCT-ACT-CG | 12 | 5' Cap region |
| 6003 | GCC-GCT-ACT-CGA-ATG-AGC-GC | 13 | 5' Cap region |
| 6004 | GGA-AGA-GCC-GCT-ACT-CGA-AT | 14 | 3' Untranslated |
| 6005 | CTC-TGT-TCC-TTT-AAT-TAC-GA | 15 | 3' Untranslated |
| 6006 | TCC-ACT-TGA-TGA-TGT-CTC-TC | 16 | 3' Untranslated |
| 6007 | CTA-TGA-TTT-CTC-TCC-ACT-TG | 17 | 3' Untranslated |

TABLE I-continued

Oligonucleotides targeted to MDR1

| ISIS # | SEQUENCES* (DESCRIPTION) | SEQ ID NO: | TARGET REGION |
|---|---|---|---|
| 6010 | GGC-AGT-CAG-TTA-CAG-TCC-AA | 18 | 3' Untranslated |
| 6011 | TTT-TAG-CAA-GGC-AGT-CAG-TT | 19 | 3' Untranslated |
| 6012 | TGC-AAA-CAT-TTC-AAT-ACT-TT | 20 | 3' Untranslated |
| 6013 | AAG-TTT-AGT-TTT-ATT-ATA-GA | 21 | 3' Untranslated |
| 10221 | CAC-CAC-CCC-CCT-CGC-TGG-TC | 22 | Scrambled #5995 |
| 10222 | CTC-CCG-CAC-ATC-TCC-GCG-CC | 23 | Scrambled #5995 |
| 11432 | GCC-ACC-GTC-TGC-CCA-CTC-TG | 24 | ORF |
| 11433 | GGC-ACG-TGC-AAT-GGC-GAT-CC | 25 | ORF |
| 11434 | CGG-AGC-CGC-TTG-GTG-AGG-AT | 26 | ORF |
| 11435 | AGC-AGC-ATC-ATT-GGC-GAG-CC | 27 | ORF |
| 11436 | CGG-CCA-TGG-CAC-CAA-AGA-CA | 28 | ORF |
| 11437 | TGA-ACT-GAC-TTG-CCC-CAC-GG | 29 | ORF |
| 11438 | GGG-ATG-TCC-GGT-CGG-GTG-GG | 30 | ORF |
| 11439 | TGC-CCA-CCA-GAG-CCA-GCG-TC | 31 | ORF |
| 11440 | ATG-CCC-AGG-TGT-GCT-CGG-AG | 32 | ORF |
| 11441 | GCC-TCC-TTT-GCT-GCC-CTC-AC | 33 | ORF |
| 11442 | TGG-TGG-ACA-GGC-GGT-GAG-CA | 34 | ORF |
| 10443 | 2'-O-Methyl analog of #5995 | 4 | Start codon |
| 10664 | CCA-TCC-CGA-CCT-CGC-GCT-CC<br>2'-F gapmer analog of #5995 | 4 | Start codon |
| 11587 | CCA-TCC-CGA-CCT-CGC-GCT-CC<br>2'-F gapmer analog of #5995 | 4 | Start codon |
| 10553 | CCA-TCC-CGA-CCT-CGC-GCT-CC<br>2'-Y gapmer analog of #5995 | 4 | Start codon |
| 11207 | CCT-GGT-CAT-GTC-TTC-CTC-CA<br>2'-Y gapmer analog of #5996 | 8 | ORF (splice junction) |
| 11206 | CTT-TGC-CCA-GAC-AGC-AGC-T̲G<br>2'-Y gapmer analog of #5997 | 9 | ORF (splice junction) |
| 11073 | 5'-Cholesterol analog of # 5995 | 4 | Start codon |
| 12064 | 5'-Cholesterol analog of # 10221 | 22 | Scrambled control for # 11073 |
| 13758 | CCA-T̲CC-CGA-CCT-CGC-GCT-CC<br>2' MOE gapmer analog of # 5995 | 4 | Start codon |
| 13753 | CAC-C̲AC-CCC-CCT-CGC-TGG-TC<br>2' MOE gapmer analog of # 10221 | 22 | Scrambled control for # 13758 |
| 13755 | GTT-C̲AC-TGG-CGC-TTT-GTT-CC<br>2' MOE gapmer analog of # 5998 | 10 | ORF / Stop codon |
| 14429 | CTT-AC̲C-CGC-TTG-TGT-TGC-TG<br>2' MOE gapmer | 37 | Scrambled control for # 13755 |
| 13756 | TTT-TAG-CAA-GGC-AGT-C̲AG-TT<br>2' MOE gapmer analog of # 6011 | 19 | 3' Untranslated |
| 13757 | TCC-AC̲T-TGA-TGA-TGT-CTC-TC<br>2' MOE gapmer analog of # 6006 | 16 | 3' Untranslated |
| 12065 | Analog of # 5995 comprising FITC at 3' end | 4 | Start codon |
| 13329 | Analog of # 5995 comprising 3'-O-pentylamino cholesterol | 4 | Start codon |
| 13330 | Analog of # 5995 w/ 5'-C6 amino linker & 3'-O-pentylamino cholesterol | 4 | Start codon |
| 13331 | Analog of # 5995 comprising 5' FITC & 3'-O-pentylamino cholesterol | 4 | Start codon |
| 13332 | Analog of # 10221 comprising 3'-O-pentylamino cholesterol | 22 | Scrambled control |
| 13409 | Analog of # 5995 comprising 5'-C6 amino linker | 4 | Start codon |
| 13434 | Analog of # 5995 comprising FITC at 5' end | 4 | Start codon |

*From left to right, sequences are written from 5' to 3'. All oligonucleotides contain fully substituted phosphorothioate backbones unless otherwise indicated. Emboldened residues comprise the indicated 2' modifications: MOE, 2'-methoxyethoxy; F, 2'-fluoro-; OF, 2'-O-fluoro; Y, 2'-propyl; C̲, 5-methyl cytosine.
**ORF, open reading frame.

Example 2
Oligonucleotide-mediated reduction of MDR1 mRNA levels

Methods: NIH 3T3 cells transfected with a plasmid containing the human MDR1 gene (pSK1 MDR) have been previously described (Kane et al., Gene, 1989, 84, 439). These cells have proven to be useful models for the study of multi-drug resistance phenomena. Cells were grown in DMEM media containing 10% fetal bovine serum (FBS) and 60 ng/ml colchicine in an atmosphere of 95% air, 5% $CO_2$.

In most cases, the multi-drug resistant 3T3 cells were exposed to oligonucleotides administered as a complex with cationic liposomes (LIPOFECTIN™). However, all studies with cholesterol conjugated oligonucleotides were performed in the absence of cationic liposomes. Cells were treated with oligonucleotides according to the following procedure. Cells were grown in 162 mm flasks. When 95% confluency was reached, cells were seeded onto 100 mm dishes at $5 \times 10^6$/dish in 10 ml of 10% FBS/DMEM and incubated for 24 hours. At this stage, the cells were washed two times with phosphate buffered saline (PBS) and then 8 ml of serum-free medium was added. For phosphorothioate oligonucleotides, 20 ug/ml LIPOFECTIN™ (GIBCO/BRL, Gaithersburg, Md.) and various amounts of oligonucleotide were mixed, pre-incubated at room temperature for 30 minutes, and then incubated with the cells at 37° C. in a $CO_2$ incubator for various periods. Similar methods were used for 2'-O-methyl phosphorothioate oligonucleotides. For treatments with cholesterol-phosphorothioate oligonucleotides, the compounds were simply added to the cells in serum free medium (in the absence of LIPOFECTIN™) with antibiotics and incubated at 37° C. in a $CO_2$ incubator for various periods. The cytotoxicity of the various treatments used in the oligonucleotide experiments were evaluated in preliminary experiments by using a vital dye assay. Unless otherwise noted, conditions were chosen such that there was usually less than a 10% difference in the number of viable cells in samples treated with oligonucleotides versus control samples maintained in medium alone. The MDR-3T3 cells maintained a high level of viability during extended incubation in serum free medium, although cell division was largely suppressed.

To measure MDR1 mRNA expression by Northern blotting, total cellular RNA was isolated by lysis in 4M guanidium isothiocyanate followed by a cesium chloride gradient, and the RNA was resolved on 1.2% agarose gels containing 1.2% formaldehyde and transferred to nitrocellulose membranes (Dean et al., J. Biol. Chem., 1994, 269, 16416). The blots were hybridized with a $^{32}P$ radiolabeled human MDR1 cDNA probe. The MDR1 cDNA probe was isolated by performing a polymerase chain reaction on the pSK1 MDR plasmid, as described previously (Alahari et al., Nucl. Acids Res., 1993, 21, 4079). The following oligonucleotide primers were used for PCR:

5'-GGATCTTGAAGGGGACCGCAATGGAGGAGC, and (SEQ ID NO: 35)

5'-GTCCAACACTAAAAGCCCCAATTAATACAG. (SEQ ID NO: 36)

The resulting fragment was checked on an agarose gel and was radiolabeled with $^{32}P$-dCTP using a commercially available random primer labeling kit (Amersham, Arlington Heights, Ill.) according to the manufacturer's instructions. The filters were hybridized overnight in hybridization buffer (25 mM $KPO_4$, pH 7.4; 5× SSC; 5× Denhardt's solution, 100 ug/ml Salmon sperm DNA and 50% formamide) (Alahari et al., Nucl. Acids Res., 1993, 21, 4079). This was followed by two washes with 1× SSC, 0.1% SDS and two washes with 0.25× SSC, 0.1% SDS. Hybridizing bands were visualized by exposure to X-OMAT AR film and quantitated using a PhosphorImager™ (Molecular Dynamics, Sunnyvale, Calif.). To confirm equal loading of RNA, the blots were stripped and reprobed with a $^{32}P$-labeled beta-actin probe (Clontech, Palo Alto, Calif.).

Identification of an antisense oligonucleotide that specifically reduces MDR1 message expression: RNA isolated from MDR 3T3 cells was probed with a 1.0 kb PCR-based MDR1 probe; this revealed a transcript of 4.4 kb. In initial experiments, the MDR 3T3 cells were exposed to 1.0 μm concentrations of several different antisense oligonucleotides, or control oligonucleotides, in the presence of 20 ug/ml LIPOFECTIN™ for 24 hours. One oligonucleotide, ISIS 5995, which was targeted to a region overlapping the AUG codon, caused over 50% reduction in MDR1 message levels. See Table II. Oligonucleotides ISIS 10221 and ISIS 10222 have the same base composition as ISIS 5995, but are "scrambled" sequences that were used as specificity controls; these control oligonucleotides caused 4% and 14% reduction respectively. NIH 3T3 cells transfected with pSK1 MDR plasmid were grown to 90% confluence and treated with oligonucleotide (1 μm) for 24 hours in the presence of LIPOFECTIN™ in serum free medium. Total RNA was isolated and fractionated on agarose formaldehyde gels and blotted onto nitrocellulose membranes. These membranes were probed with a $^{32}P$ radiolabeled 1.0 kb MDR1 cDNA, and then stripped and reprobed with a $^{32}P$ radiolabeled beta-actin cDNA probe to confirm equal loading of RNA, allowing the levels of MDR1 transcripts to be normalized with regard to the beta-actin bands. Transcript levels were quantitated using a PHOSPHORIMAGER™ (Molecular Dynamics, Sunnyvale, Calif); the values are expressed in arbitrary units (the beta-actin transcripts were essentially constant).

TABLE II

MODULATION OF MDR1 mRNA BY ANTISENSE OLIGONUCLEOTIDES

| ISIS No. | SEQ ID NO: | MDR1 mRNA Level (arbitrary units) | % Control |
| --- | --- | --- | --- |
| None* | — | 473,913 | 100% |
| LIPOFECTIN ™ | — | 430,435 | 91% |
| 5990 | 1 | 443,478 | 94% |
| 5995 | 4 | 226,087 | 48% |
| 10221 | 22 | 456,522 | 96% |
| 10222 | 23 | 406,522 | 86% |

*Control = untreated cells

This experiment was repeated several times, and the MDR1 and beta-actin bands on non-saturated autoradiograms were compared by laser densitometry. The MDR1/beta-actin ratios for the ISIS 5995 and ISIS 10221 oligonucleotides were 0.49 and 1.01, respectively, indicating specific inhibition of MDR1 message levels by ISIS 5995.

In additional experiments, all of the phosphorothioate oligonucleotides listed in Table I were screened for their ability to reduce MDR1 message levels when used at 1.0 μM concentration with cationic liposome. Of these phosphorothioate oligonucleotides, ISIS 5995 was the most effective, consistently causing about 50% reduction in MDR1 message levels.

Time course of inhibition of MDR1 message levels by oligonucleotide ISIS 5995: In order to evaluate the time course of ISIS 5995-mediated MDR1 modulation, transfected cells were treated with 1 μm ISIS 5995, or 1 μm ISIS 10221, for 24, 48 and 72 hours. MDR1 and beta-actin RNA levels were examined as described above. Maximum specific reduction of MDR1 mRNA was observed after 24 hours treatment of cells with ISIS 5995; longer treatment did not result in lower mRNA levels. With these unmodified oligonucleotides, reduction of MDR1 mRNA levels was attained only when oligonucleotide treatment was performed in serum free medium, and when cationic liposomes were used. This result is consistent with previous observations on antisense actions of phosphorothioate oligonucleotides in cell culture (Bennett et al., *Mol. Pharm.*, 1992, 41, 1023; Manoharan et al., *Tetrahedron Lett.*, 1995, 36, 3651). Multiple treatments with ISIS 5995 oligonucleotide did not cause any greater specific reduction in MDR1 message levels than a single treatment, while greater cytotoxicity was observed. The reduction in MDR1 mRNA expression was reversible, since, after 24 hours exposure to ISIS 5995, cells returned to culture medium without oligonucleotide demonstrated normal levels of MDR1 mRNA within 24 hours.

Concentration dependence of MDR1 message reduction: Treatment of multi-drug resistant 3T3 cells with oligonucleotide ISIS 5995 resulted in a concentration-dependent inhibition of MDR1 message. Reduction in message levels was observed with concentrations as low as 100 nM. Maximal specific effects were observed at approximately 1.0 $\mu$m; this entailed an approximately 60% reduction in MDR1 message. Use of higher concentrations of oligonucleotides (5–10 $\mu$m) with LIPOFECTIN™ resulted in greater non-specific effects, i.e., reduced beta-actin message levels and increased cytotoxicity, which were observed with both ISIS 5995 and ISIS 10221 (the scrambled control).

Example 3
Oligonucleotide-mediated inhibition of P-glycoprotein

Methods: Transfected MDR NIH 3T3 cells were grown and treated with oligonucleotides as described in Example 2. In order to measure P-glycoprotein expression by Western blotting, cells were seeded in 60 mm dishes at $1.2 \times 10^6$ per dish and incubated for 24 hours in serum containing medium. The cells were treated with the oligomers for various times in serum free medium as described above. Cells were then extracted in lysis buffer (20 mM Tris, pH 7.5, 2 mM EDTA, 500 mM EGTA, 2 mM PMSF, 1 mM DTT, aprotonin (10 ug/ml), 0.5% Triton-X) and sonicated briefly. The lysate was spun in a microfuge tube for 20 minutes at 4° C. and the resulting supernatant was checked for protein content. Equal amounts of protein (usually 20 ug) were mixed with SDS sample buffer and boiled. Protein samples were separated by 8% SDS PAGE and the resolved proteins were electrophoretically transferred onto polyvinylidene fluoride membranes (Millipore, Bedford, Mass.). The membranes were blocked (with 3% BSA, 2% non fat dry milk in PBS) and then treated with 2 ug/ml C219 anti-P-glycoprotein antibody (Signet, Dedham, Mass.). After washing three times with 0.1% Tween 20, the membranes were incubated with rabbit anti-mouse antibody (Cappel, Durham, N.C.). Immunoreactive proteins were visualized either by ECL (Enhanced Chemiluminescence, Amersham, Arlington Heights, Ill.) or with $^{125}$I secondary antibodies.

Results: The effect of ISIS 5995 on P-glycoprotein expression was evaluated by Western blot analysis. Consistent with the Northern blot analyses of mRNA levels, expression of the P-glycoprotein was reduced upon treatment of the multidrug resistant 3T3 cells with the ISIS 5995 oligomer. In the Western assays, P-glycoprotein was reduced at least 80% by treatment with ISIS 5995 and about 50% by ISIS 10440. In contrast, scrambled control oligomer ISIS 10221 did not reduce P-glycoprotein expression. The decrease in P-glycoprotein expression was minimal after 24 hours, readily detectable by 48 hours, and reached a maximum only after 72 hours exposure. Thus, effects at the protein level lag behind the observed reduction in message levels. This observation is consistent with the fact that the P-glycoprotein is quite stable and normally turns over rather slowly with a t1/2 of 48–72 hours (Richert et al., *Biochem.*, 1988, 28, 7607).

Example 4
Effects of a cholesterol derivative of oligonucleotide 5995 on MDR1 message levels and P-glycoprotein expression A 5'-cholesterol derivative of ISIS 5995 (ISIS 11073), as well as a 5'-cholesterol derivative of the scrambled control oligonucleotide ISIS 10221 (ISIS 12064), were synthesized and their effects on MDR1 message and P-glycoprotein levels were examined. As is explained below, 3'-cholesterol derivatives were also prepared and tested.

Methods: Transfected MDR NIH 3T3 cells were grown and treated with oligonucleotides as described in Example 2. MDR1 mRNA expression was measured by Northern blotting as described in Example 3. In order to measure cell surface P-glycoprotein levels by flow cytometry, cells were seeded in 60 mm dishes at $1.2 \times 10^6$/plate in 5 ml of medium, grown for one day in 10% FBS/DMEM, and exposed to the oligomers in serum free medium. After treatment with the oligonucleotides, cells were washed twice in PBS, 0.25 ml of pancreatin was added to remove cells from the plate, and the dispersed cells were resuspended in 10% FBS/DMEM and incubated at 37° C. for 2 hours. After the incubation, cells were washed in PBS, and 50 $\mu$l of 20 ug/ml MRK16 anti-P-glycoprotein antibody (Kamiya, Thousand Oaks, Calif.) was added (Ishida et al., *Jpn. J. Cancer Res.*, 1989, 80, 1006). This mixture was incubated for 45 minutes on ice and cells were washed three times in 10% FBS/PBS. Cells were then incubated for 30 minutes with 20 $\mu$l of ten times diluted secondary antibody, a R-phycoerythrin (R-PE) conjugated goat anti-mouse IgG (Sigma, St. Louis, Mo.). After the incubation, cells were washed two times in 10% FBS/PBS. Finally, the cells were resuspended in 500 $\mu$l of PBS. The level of R-PE fluorescence in viable cells (as determined by light scatter) was quantitated using the Cicero software application (Cytomation, Fort Collins, Colo.) on a Becton Dickinson flow cytometer.

Results: As shown in Table III, treatment with concentrations of ISIS 11073 (cholesterol 5995) in the 250 nM to 2.5 $\mu$m range, resulted in a specific decrease in levels of MDR1 message. It is important to note that at least about 60% inhibition of MDR1 mRNA expression was attained with ISIS 11073 without the use of cationic liposomes.

TABLE III

MODULATION OF MDR1 mRNA BY CHOLESTEROL-CONJUGATED ANTISENSE OLIGONUCLEOTIDES

| ISIS No. | SEQ ID NO: | Conc. | Ratio of MDR1 mRNA to beta-actin mRNA |
|---|---|---|---|
| None* | — | — | 1.00 |
| 12064 | 22 | 2.5 uM | 1.10 |
| 11073 | 4 | 250 nM | 0.48 |
| 11073 | 4 | 500 nM | 0.38 |
| 11073 | 4 | 1.0 uM | 0.45 |
| 11073 | 4 | 2.5 uM | 0.59 |

*Control = untreated cells

To observe the effects of the 5'-cholesterol 5995 (ISIS 11073) oligonucleotide on the expression of P-glycoprotein at the cell surface, immunofluorescent staining and flow cytometry were utilized. Treatment of multidrug resistant 3T3 cells with increasing concentrations of ISIS 11073 over the range of 0.5–2.5 μm resulted in a progressive reduction in surface expression of P-glycoprotein to about 40% of control levels. Some non-specific reduction of P-glycoprotein expression was also observed with the scrambled control oligomer (5'-cholesterol 10221, ISIS 12064), but the effect of the antisense compound was greater at all concentrations tested. In a parallel experiment, the effect of 1 μm ISIS 5995 or ISIS 10221 administered with LIPOFECTIN™ on P-glycoprotein surface expression was examined. The test concentrations of antisense agent ISIS 5995 and the scrambled sequence ISIS 10221, administered with LIPOFECTIN™, were equal to or less effective than an equivalent concentration of the cholesterol-conjugated analogs administered without LIPOFECTIN™. Further, the cholesterol oligonucleotides showed less experiment-to-experiment variation than did the standard phosphorothioate oligonucleotides when the latter were administered with cationic lipids and are thus preferred.

To observe the effects of the 3'-cholesterol 5995 (ISIS 13329) on the expression of P-glycoprotein at the cell surface, immunofluorescent staining and flow cytometry were utilized as described above. Treatment of multidrug resistant 3T3 cells with increasing concentrations of ISIS 13329 over the range of 0.5–2.5 μm resulted in a progressive reduction in surface expression of P-glycoprotein to about 50% of control levels. In a parallel experiment, the effect of 1 μm ISIS 5995 or ISIS 13332 administered with LIPOFECTIN™ on P-glycoprotein surface expression was examined. The test concentrations of antisense (ISIS 5995) or scrambled 3'-cholesterol (ISIS 13332) phosphorothioate oligonucleotides administered with LIPOFECTIN™, were less effective than an equivalent concentration of the cholesterol-conjugated analogs administered without LIPOFECTIN™. Further, the cholesterol oligonucleotides showed less experiment-to-experiment variation than did the standard phosphorothioate oligonucleotides when the latter were administered with cationic lipids. The 3'-cholesterol oligonucleotide are also stable against 3'-exonucleases.

Example 5
Uptake and intracellular distribution of oligonucleotides

As Example 4 demonstrates, the 3'-cholesterol derivative of ISIS 5995 (ISIS 13329) had similar effects on P-glycoprotein expression to the 5'-cholesterol derivative of 5995 (ISIS 11073). To determine the rate of cellular uptake and intracellular distribution of MDR1 antisense oligonucleotides, the following experiments were performed with 5'-FITC, 3'-cholesterol oligonucleotides.

Methods: The cellular accumulation of FITC labeled oligonucleotides was quantitated by flow cytometry. The cell uptake and intracellular distribution were visualized on a cell-by-cell basis using digitized fluorescence microscopy, essentially as described previously (Shoji et al., *Nucl. Acids Res.*, 1991, 19, 5543), except that a confocal microscope system was used. Intracellular fluorescence was visualized by taking optical sections through the cell body; a section approximately half way between the top surface of the cells and the surface of the cover slip was examined in each case. Phase contrast images of the same cells were also obtained. A Nikon Fluor 40/1.3 Oil Ph4DL objective was used, with Comos software controlling a Biorad MRC600 scanner/laser. In digitized images, gain and black level settings were optimized on cells treated with free FITC 5995 oligomer and were unchanged thereafter.

Incubation conditions for the flow cytometry and confocal microscopy experiments were as follows. MDR 3T3 cells were treated with 1 μm ISIS 13331 (5'-FITC, 3'-cholesterol 5995), or with 1 μm ISIS 13434 (5'-FITC 5995) with or without LIPOFECTIN™, for either 2 hours or 18 hours in serum free medium at 37° C. Cells were harvested and the fluorescence profiles were determined using a flow cytometer; light scatter parameters were set so as to exclude non-viable cells. In the case of the 18 hour treatment with LIPOFECTIN™ there were some cells with very high levels (above $10^4$ units) of fluorescence; these were accumulated in one channel. Cells plated on glass coverslips were treated as above for 18 hour and then examined by confocal microscopy as described above.

Results: During a 2 hour incubation period the cholesterol conjugated oligonucleotide (ISIS 13331) was rapidly accumulated by cells, while both free ISIS 13434, and ISIS 13434 complexed with LIPOFECTIN™, accumulated to a far lesser degree. The cellular accumulation of the 3'-cholesterol conjugated 5995 (ISIS 13331) was approximately 40 fold greater than ISIS 13434 at 2 hours. After overnight incubation, the free ISIS 13434 still displayed significantly less cell accumulation than ISIS 13331. The LIPOFECTIN™ complexed ISIS 13434 displayed substantial, but very heterogeneous, cell uptake after overnight incubation. Based on previous experience with stability of phosphorothioates (Akhtar et al., *Trends in Cell Biology*, 1992, 2, 139) it is believed that most of the fluorescence accumulated represents FITC-conjugated oligonucleotide rather than free FITC.

Confocal microscopic images essentially confirmed and extended the flow cytometry observations. Very little intracellular accumulation was seen with ISIS 13434. The cells treated with ISIS 13434 complexed with LIPOFECTIN™ showed extensive, but very heterogeneous, cellular uptake, with some cells heavily stained and others essentially blank; there was also a background of LIPOFECTIN™ particles plus associated oligonucleotide bound to the cover slip. Some of the cells treated with LIPOFECTIN™ showed nuclear accumulation of the fluorescence. The cells treated with ISIS 13331 (5'-FITC, 3'-cholesterol) oligonucleotide uniformly displayed extensive fluorescence in both the cytoplasm and nucleus. These observations demonstrate that the cholesterol conjugation has enhanced the rapidity, amount, and uniformity of cellular uptake of the oligonucleotide, and leads to substantial cytoplasmic and nuclear accumulation.

Example 6
Effects of oligonucleotides on Rh 123 accumulation

Rhodamine 123 is a fluorescent dye that is a substrate for P-glycoprotein and is rapidly transported out of multi-drug resistant cells. Thus, Rh 123 uptake can be employed as a simple and convenient way of assessing the impact of various treatments on the multi-drug resistance phenotype.

Methods: In order to measure Rhodamine 123 uptake by flow cytometry, the procedure described by Twentyman et al. (*Eur. J. Cancer*, 1994, 30, 1360) was followed with minor changes. Briefly, 7.5×10⁵ cells were seeded on 6 well plates, incubated for one day, and treated with oligomers as described above. Cells were removed with pancreatin and resuspended in 10% FBS/DMEM. Rhodamine 123 (Sigma, St. Louis, Mo.) was dissolved in water, added to a final concentration of 1.0 ug/ml; 500 μl samples were taken at several points, washed with medium once, and resuspended in 500 μl of media. Viable cells were analyzed for the accumulation of Rhodamine 123 on a Becton Dickinson flow cytometer using Cicero software.

Results: Treatment of multi-drug resistant 3T3 cells with increasing concentrations of ISIS 11073 (cholesterol-conjugated ISIS 5995) resulted in a progressive decrease in P-glycoprotein expression that paralleled an increase in Rh 123 accumulation. As in the case of P-glycoprotein expression, some non-specific effect was also observed with the scrambled control oligomer (ISIS 12064; cholesterol-conjugated ISIS 10221); however, the effect of the antisense compound was significantly greater. A parallel experiment showed that standard phosphorothioate oligomers, given with cationic liposomes, also had effects on Rh 123 accumulation, but a lesser discrimination between antisense and scrambled sequences was observed.

Example 7
Effects of 2'-methoxyethoxyoligonucleotides on P-glycoprotein expression Methods: 2'-Methoxyethoxy derivatives of ISIS 5995 (ISIS 13758, targeted to the start codon region of MDR1), ISIS 5998 (ISIS 13755, targeted to the stop codon region of MDR1) and ISIS 10221 (ISIS 13753, a scrambled control for ISIS 5995) were prepared and examined for their ability to modulate P-glycoprotein expression. To assay activity, experiments were conducted essentially as described in Example 6. These oligonucleotides are "chimeric" or "gapped" compounds having 2'-methoxyethoxy modifications on the five 5' and five 3' nucleotides, wherein each methoxyethoxy cytosine is a 5-methyl cytosine, and phosphorothioate deoxynucleotides in the center ten nucleotides of the molecules. This configuration allows the oligonucleotide to have nuclease-resistant "wings" while retaining a central portion that supports the action of RNase H.

Results: The 2'-methoxyethoxy derivative of ISIS 5995 (ISIS 13758) inhibited P-glycoprotein expression. ISIS 13755, the 2'-methoxyethoxy derivative of ISIS 5998, also exhibited activity in these assays (i.e., 60% inhibition of MDR1 protein), even though the phosphorothioate oligonucleotide ISIS 5998 had little or no effect on MDR1 mRNA expression. These results are an example of the enhanced efficacy of oligonucleotide activity that can be achieved by incorporating methoxyethoxy modifications into oligonucleotides. Although not wishing to be bound by any particular theory, these results are believed to demonstrate the enhanced activity resulting from the ability of methoxyethoxy modifications to render oligonucleotides resistant to many nucleases, as well as their ability to increase the hybridization affinity of oligonucleotides to their targeted nucleic acid (i.e., RNA or DNA) molecules.

Example 8
Effects of 3'-cholesterol, 2'-methoxyethoxy gapmer oligonucleotides on P-glycoprotein expression Cholesterol is conjugated to ISIS 13758 (2'-methoxyethoxy targeted to the translation start codon region), ISIS 13753 (2'-methoxyethoxy scrambled control for ISIS 13758) , ISIS 13755 (2'-methoxyethoxy targeted to the translation termination codon region) and ISIS 14429 (2'-methoxyethoxy scrambled control for ISIS 13755) using 3'-O-[pentylamino-carbonyl-oxy-cholesteryl]-cytidine CPG as described above. Biological assays are conducted as described in the previous examples. These phosphorothioate oligonucleotides are chimeric compounds having a 3'-cholesterol (for cellular uptake and nuclease resistance) 2'-methoxyethoxy modifications in their flanks (for better binding to the target nucleic acid and for nuclease resistance), and 2'-deoxy nucleotides in the center 10 nucleotide region (the "gap"). This configuration allows the chimeric oligonucleotide to have nuclease-resistant, high affinity "wings" while retaining an unmodified central "gap" that supports the action of RNase H when the oligonucleotide is bound to a target RNA molecule. Placing the cholesterol moiety at the 3'-terminus of the 3' oligonucleotide ensures resistance to 3' exonucleases, enhances cellular uptake, and leaves the 5'-terminus available for conjugation of additional functional groups. Exemplary sequences having this configuration are depicted in Table IV.

TABLE IV

3'-Cholesterol, 2'-Methoxyethoxy Gapmer Oligonucleotides

| ISIS # | SEQUENCE/STRUCTURE | SEQ ID NO: |
|---|---|---|
| 10221 (scrambled 5995) | CACCA CCC CCC TCGC TGGTC<br>All PS | 22 |
| 16266 | CACCA CCC CCC TCGC UGGUC#<br>All PS | 38 |
| 13753 | CACCA CCC CCC TCGC UGGUC^<br>All PS | 38 |
| 16302 | CACCA CCC CCC TCGC UGGUC#<br>All PS | 38 |
| 16304 | CACCA CCC CCC TCGC UGGUC#<br>All PS | 38 |
| 5995 (MDR1 active) | CCATC CCG ACC TCGC GCTCC<br>All PS | 4 |
| 16298 | CCAUC CCG ACC TCGC GCUCC#<br>All PS | 39 |
| 16300 | CCAUC CCG ACC TCGC GCUCC^<br>All PS | 39 |
| 16301 | CCAUC CCG ACC TCGC GCUCC#<br>PO      PS      PO | 39 |
| 16303 | CCAUC CCG ACC TCGC GCUCC^<br>PO      PS      PO | 39 |
| 5998 (MDR1 active) | GTTCA CTG GCG CTTT GTTCC<br>All PS | 10 |
| 13755 | GUUCA CTG GCG CTTT GUUCC<br>All PS | 40 |
| 16611 | GUUCA CTG GCG CTTT GUUCC#<br>PO      PS      PO | 40 |
| 16612 | GUUCA CTG GCG CTTT GUUCC^<br>PO      PS      PO | 40 |
| 16615 | GUUCA CTG GCG CTTT GUUCC#<br>All PS | 40 |
| 14429 (scrambled 13755) | CTTAC CCG CTT GTGT TGCTG | 37 |
| 16613 | CUUAC CCG CTT GTGT UGGUC#<br>All PS | 41 |
| 16614 | CUUAC CCG CTT GTGT UGGUC^<br>All PS | 41 |
| 16616 | CUUAC CCG CTT GTGT UGGUC#<br>PO      PS      PO | 41 |
| 16617 | CUUAC CCG CTT GTGT UGGUC^<br>PO      PS      PO | 41 |

What is claimed:

1. An oligonucleotide slected from the group consisting of SEQ ID NO: 2, 3, 4, 5, 6, 7, 8, 9, 11, 12, 13, 14, 15, 16, 17, 18, 19, 20, 21, 24, 25, 26, 27, 28, 29, 30, 32, 33, 34, 39 and 40, wherein said oligonucleotide inhibits the expression of P-glycoprotein.

2. An oligonucleotide selected from the group consisting of SEQ ID NO: 2, 3, 4, 5, 6, 7, 8, 9, 10, 11, 12, 13, 14, 15, 16, 17, 18, 19, 20, 21, 24, 25, 26, 27, 28, 29, 30, 32, 33, 34, 39 and 40, wherein said oligonucleotide inhibits the expression of P-glycoprotein and wherein said oligonucleotide comprises at least one 2' methoxyethoxy modification, a cholesterol moiety or a 3' terminal cytidylate residue wherein said 3' terminal cytidylate residue comprises a 3'-O-alkylamino linkage to a lipophilic moiety wherein said lipophilic moiety enhances the cellular uptake of said oligonucleotide.

3. A pharmaceutical composition comprising the oligonucleotide of claim 1 and a pharmaceutically acceptable carrier.

4. The oligonucleotide of claim 2 wherein said lipophilic moiety is selected from the group consisting of a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety.

5. The oligonucleotide of claim 2 wherein said 3' terminal cytidylate residue is selected from the group consisting of 2'-deoxycytidylate, 5-methyl cytidylate, 2' deoxy-5-methyl cytidylate, 2'-0-methoxyethoxycytidylate and 5-methyl 2'-0-methoxyethoxycytidylate.

6. A pharmaceutical composition comprising the oligonucleotide of claim 2 and a pharmaceutically acceptable carrier.

* * * * *

UNITED STATES PATENT AND TRADEMARK OFFICE
CERTIFICATE OF CORRECTION

PATENT NO. : 6,001,991
DATED : December 14, 1999
INVENTOR(S): Dean et al.

It is certified that error appears in the above-identified patent and that said Letters Patent is hereby corrected as shown below:

At Col. 4, Line 55, please delete "c-myb U.S. Pat. No." and insert therefor --c-myb gene U.S. Pat. No.--

At Col. 6, Line 21, please delete "$O-CH_2$). Also preferred" and insert therefor --$O-CH_2$. Also preferred--

At Col 15, Line 25, please delete "37°C." and insert therefor --37°C--

At Col. 15, Line 31, please delete "37°C." and insert therefor --37°C--

At Col. 17, Line 45, please delete "4°C." and insert therefor --4°C--

At Col. 18, Line 29, please delete "37°C." and insert therefor --37°C--

Signed and Sealed this

Twentieth Day of March, 2001

Attest:

NICHOLAS P. GODICI

Attesting Officer        Acting Director of the United States Patent and Trademark Office